US007771758B2

(12) United States Patent
Gafner et al.

(10) Patent No.: US 7,771,758 B2
(45) Date of Patent: Aug. 10, 2010

(54) EXTRACT OF MAD-DOG SKULLCAP

(75) Inventors: Stefen Gafner, Kennebunkport, ME (US); Chantal Bergeron, Kennebunkport, ME (US); Fiona Elizabeth Russell, Kennebunkport, ME (US)

(73) Assignee: Tom's of Maine, Kennebunk, ME (US)

( * ) Notice: Subject to any disclaimer, the term of this patent is extended or adjusted under 35 U.S.C. 154(b) by 0 days.

(21) Appl. No.: 11/652,198

(22) Filed: Jan. 11, 2007

(65) Prior Publication Data

US 2007/0190189 A1 Aug. 16, 2007

Related U.S. Application Data

(62) Division of application No. 10/655,935, filed on Sep. 5, 2003, now abandoned.

(60) Provisional application No. 60/408,940, filed on Sep. 6, 2002.

(51) Int. Cl.
*A61K 36/539* (2006.01)

(52) U.S. Cl. .................................... 424/741

(58) Field of Classification Search ........................ None
See application file for complete search history.

(56) References Cited

U.S. PATENT DOCUMENTS

| 2,774,714 | A | * | 12/1956 | Hershberg et. al. | |
|---|---|---|---|---|---|
| 6,210,738 | B1 | * | 4/2001 | Chen | 426/597 |
| 6,444,218 | B2 | * | 9/2002 | Han et al. | |
| 6,608,102 | B1 | | 8/2003 | Howell et al. | |
| 6,740,343 | B2 | | 5/2004 | Wolfson et al. | |
| 2003/0165588 | A1 | | 9/2003 | Jia et al. | |

OTHER PUBLICATIONS

I Hutchens, A. R., A Handbook of Native American Herbs (1992). Shambhala Publications, Inc. (USA), pp. 172-174: "Skullcap, *Scutellaria laterfolia*".*

Burlage, HM, (1968) Index of Plants in Texas with Reputed Medicinal and Poisonous Properties, Coll. Pharm Univ. Texas, Austin.
Millspaugh, CF, (1974) *Scutellaria*, in: American Medicinal Plants. Dover Publications, NY, pp. 469-472.
Yaghmai, MS (1988) Flay. Frag. J. 3:27-31.
Bruno, M, et al., (1998) Phytochemistry 48:687-691.
Gafner, S, et al., (2003) in: Abstracts of Plenary Lectures and Posters, 44th Annual Meeting of the Am. Soc. of Pharm (ASP), Chappel Hill, 2003.
Liao, JF, et al., (1998) Planta Med. 64:571-572.
Hui, KM, et al., (2000) Planta Med. 66:91-93.
Gafner, S, ei al., (2003) J. Nat. Prod. 66:535-537.
Kim, DH, et al., (1998) Arch. Pharm. Res. 21:17-23.
Akao, T, et al., (2000) Pharm. Pharmocol. 52:1563-1568.
Green et al., "The Herbal Medicine-Maker's handbook: A Home Manual," The Crossing Press (2000).
Sheu SJ et al., "Analysis and Processing of active principles in Chinese Herbs III Assay on Scutellariae Radix;" Taiwan Yaoxue Zazhi (1982) 34:2 pp. 179-185 Abstract.
Charaux, C. et al, "Baicalin in leaves of Scutellaria columnae All;" Journal de Pahrmacie et de Chimie (1941) 1 pp. 401-403.
Woleson, PE, et al. An Investigation into the Efficacy of Scutellaria Lateriflora in Healthy Volunteers, Alternative Therapies, Mar./Apr. 2003, vol. 9, No. 2, 74-78, InnoVision Communications, CA.
Liao, JF, et al., Anxiolytic-like effects of baicalein and balcalin in the Vogel conflict test in mice, European Journal of Pharmacology 464, Jan. 31, 2003, pp. 141-146, Elsevier Science.
Nishikawa K. et al., Nat Med (1999), 53(4):209-213. Phenolics in tissue cultures of Scutellaria (Mar. 29, 2010).
Wang, Hy, et al., Structure-Activity Relationships of Flavonoids, Isolated from Scutellaria baicalensis, Binding to Benzodiazepine Site of Gaba a Receptor Complex, Planta Med. 2002, vol. 68, pp. 1059-1062 Georg Thienne Verlag Stuttgart, New York (Mar. 29, 2010).

* cited by examiner

*Primary Examiner*—Michele Flood
(74) *Attorney, Agent, or Firm*—Nikhil A. Heble

(57) ABSTRACT

An extract of *Scutellaria lateriflora* L. having a content of flavonoids, calculated as the sum of baicalein, scutellarin, dihydrobaicalin, ikonnikoswide I, lateriflorin, baicalein, lateriflorein and wogonin, of at least 18% by weight. A method of obtaining such an extract includes combining dried *Scutellaria lateriflora* L. plant material with a solvent.

6 Claims, 1 Drawing Sheet

EXTRACT OF MAD-DOG SKULLCAP

BACKGROUND OF THE INVENTION

This invention relates generally to extracts of Mad-dog skullcap and to methods for obtaining such extracts.

Mad-dog skullcap (*Scutellaria lateriflora* L., Lamiaceae) is a perennial herb indigenous to North America, growing in wet places from Canada to Florida and westward to British Columbia, Oregon and New Mexico. It derives its common name from the helmet-shaped upper lid of the seed pods. The aqueous extract of the flowering parts has been traditionally used by Native Americans as a nerve tonic and for its sedative and diuretic properties (Burlage H M, (1968) Index of the Plants in Texas with Reputed Medicinal and Poisonous Properties, Coll. Pharm. Univ. Texas, Austin; and Millspaugh C F, (1974) Scutellaria, in: American Medicinal Plants. Dover Publications, New York, pp. 469-472). Due to the lack of scientific studies on the plant, the use of skullcap has been very controversial.

Work on the chemistry of *S. lateriflora* has been performed only recently. Mono- and diterpenes (Yaghmai M S, (1988) Flav. Frag. J. 3: 27-31; and Bruno M, Cruciata M, Bondi M L, Piozzi F, De la Torre M C, Rodriguez B, Servettaz O, (1998) Phytochemistry 48: 687-691) have been reported as well as the flavonoids baicalin, baicalein, ikonnikoside I, scutellarin, lateriflorin (5,6,7-trihydroxy-2'-methoxyflavone-7-O-glucuronide), lateriflorein (5,6,7-trihydroxy-2'-methoxyflavone), oroxylin A-7-O-glucuronide, oroxylin A, wogonoside and wogonin (Gafner S, Kelly L, Bergeron C, Gauthier R and Angerhofer C K, in: Abstracts of plenary lectures and posters, 44nd Annual Meeting of the American Society of Pharmacognosy (ASP), Chappell Hill, 2003: poster P228). Several of these flavones, isolated from the Baikal skullcap (*Scutellaria baicalensis*) have been evaluated for their ability to bind to the benzodiazepine site of the GABAA receptor. Baicalein and baicalin are weak ligands of this receptor, but wogonin and oroxylin A showed a strong affinity in these in vitro assays. (Liao J F, Wang H H, Chen M C, Chen C C and Chen C F, (1998) Planta Med. 64: 571-572; Hui K M, Wang X H and Xue H, (2000) Planta Med. 66: 91-93; and Wang H Y, Hui K M, Chen Y, Xu S, Wong J T F and Xue H). In another in vitro assay, several flavonoids from *Scutellaria lateriflora* have been able to bind to the 5-$HT_7$ receptor (Gafner S, Bergeron C, Batcha L L, Reich J, Arnason J T, Burdette J E, Pezzuto J M and Angerhofer C K, (2003) J. Nat. Prod. 66:535-537).

Accordingly, it is desirable to develop useful extracts of Mad-dog skullcap and effective methods for obtaining such extracts.

SUMMARY OF THE INVENTION

The above-mentioned need is met by the present invention, which provides an extract of *Scutellaria lateriflora* L. (and method of obtaining the extract) having a content of flavonoids, calculated as a sum of baicalin, scutellarin, dihydrobaicalin, ikonnikoside I, lateriflorin, baicalein, lateriflorein and wogonin, of at least 18% by weight. In another embodiment, the extract is combined with a stabilizing agent such as ascorbic acide, citric acid or a combination of citric acid and ascorbic acid.

The present invention and its advantages over the prior art will be more readily understood upon reading the following detailed description and the appended claims with reference to the accompanying drawings.

DESCRIPTION OF THE DRAWINGS

The subject matter that is regarded as the invention is particularly pointed out and distinctly claimed in the concluding part of the specification. The invention, however, may be best understood by reference to the following description taken in conjunction with the sole accompanying drawing FIGURE which shows a plot of total flavonoids over time for a series of Mad-dog skullcap extracts.

DETAILED DESCRIPTION OF THE INVENTION

Figure 1:
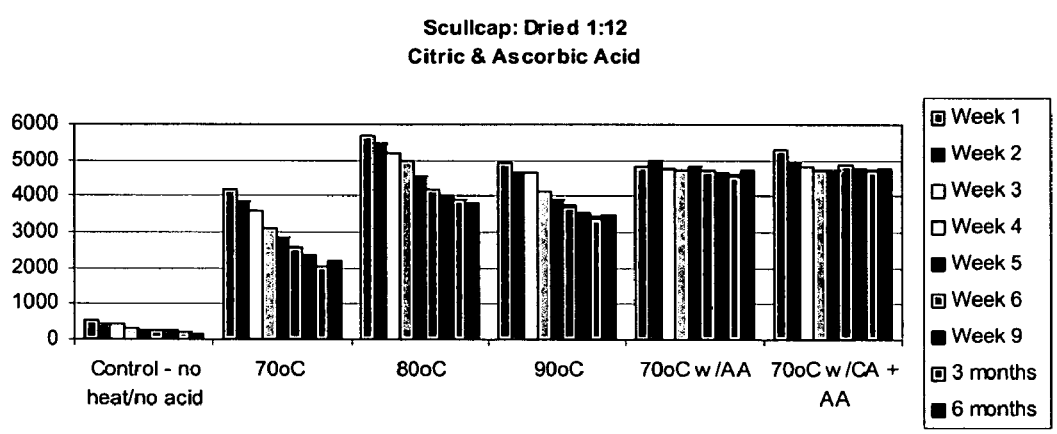

The present invention relates to flavonoid-rich extracts of Mad-dog skullcap and methods for obtaining such extracts. The following preparations and examples are given by way of illustration only, and are not to be construed as limiting.

Example 1

Preparation of a Flavonoid Rich Mad-dog Skullcap Extract

Mad-dog skullcap extracts were obtained as follows. Dried *Scutellaria lateriflora* L. herb was obtained from Blessed Herbs (Oakham, Mass.). The aboveground parts were extracted with either 70% alcohol (ratio plant material-solvent 1:10) for 24 hours or hot water (ratio plant material-solvent 1:20) for 15-30 minutes on a platform shaker.

More specifically, the hot water extraction process comprises combining one part of plant material (*Scutellaria lateriflora* L., cut and dried) with 20 parts of boiling water. The plant material comprises dried and ground aboveground parts of *Scutellaria lateriflora* L. herb. This is mixed with the ionized water which is initially boiling at 90° C.±5° C. under constant stirring for approximately 15-30 minutes. The stirring can be accomplished with a platform shaker operating at 150 rpm.

The mixture of plant material and water is filtered to separate the spent plant material from the aqueous solution. The final extract is obtained by freeze-drying the aqueous solution to remove the water. For its efficacy, it is preferred that the extract contain more than 18% by weight flavonoids, calculated as the sum of baicalin, scutellarin, dihydrobaicalin, ikonnikoside I, lateriflorin, baicalein, lateriflorein and wogonin. More particularly, the extract should contain approximately 8-9% by weight of baicalin.

Results of a recent publication (Gafner S, Bergeron C, Batcha L L, Reich J, Arnason J T, Burdette J E, Pezutto J M and Angerhofer C K, (2003) J. Nat. Prod. 66:535-537) showed that the hot water and 70% alcohol extracts both were able to bind to the 5-$HT_7$ receptor. From the results obtained in the testing of the pure compounds it is evident that this activity is at least partly due to the presence of flavonoids.

This extract (unmodified) has also shown in vitro activity against cyclooxygenase-1 (COX-1) and cyclooxygenase-2 (COX-2).

The presence of a large amount of flavone-7-O-glucuronides is very interesting in the light of recent findings indicating that baicalin is transformed to its aglycon baicalein by intestinal bacteria (Kim D H, Jung E A, Sohng I S, Han J A, Kim T H, Han M J (1998) Arch. Pharm. Res. 21: 17-23). Baicalein is readily absorbed intestinally but is efficiently conjugated back to baicalin in the plasma (Akao T, Kawabata K, Yanagisawa E, Ishihara K, Mizuhara Y, Wakui Y, Sakashita Y, Kobashi K, (2000) J. Pharm. Pharmacol. 52: 1563-1568). It is possible that other flavone-7-O-glucuronides are absorbed in a similar way. It remains to confirm, however, the extent to which a compound is able to cross the blood-brain barrier.

Example 2

Preparation of Mad-dog Skullcap Extract with Enhanced Flavonoid Stability

Because flavonoids found in skullcap extracts have been shown to be extremely unstable, steps to enhance flavonoid stability are proposed. The inventors' research has shown that dried *S. lateriflora* extracts result in better flavonoid extraction and more stable extracts than fresh extracts. Heating (to at least 70° C.) improved flavonoid extraction of total initial flavonoids by 10-fold. Over time, however, the flavonoids in such extracts can still degrade extensively. The following preparations illustrate the use of stabilizing agents (e.g., ascorbic acid or a combination of citric acid and ascorbic acid) to stabilize the flavonoids in *S. lateriflora* extracts for use in medicinal preparations in the herbal industry. It is also possible to use only citric acid as a stabilizing agent.

Generally, dried *S. lateriflora* was extracted (w/v) using heat (70° C., 80° C., and 90° C.), heat (70° C.) with ascorbic acid (0.5% w/w solvent) and, heat (70° C.) with citric acid and ascorbic acid (0.45%, 0.05%, respectively w/w solvent). In each case, 10 mL of solvent (35% water/65% glycerin) was added for every gram of skullcap herb. Water was heated to boiling then weighed and the herb was added. The appropriate heat (70, 80 or 90° C.) was maintained and held for 25 minutes. Covers were placed on the beakers to ensure minimal evaporation. The glycerin portion was weighed and stirred into the macerate for a further 5 minutes without additional heat. The macerate was allowed to cool and, for the samples using stabilizing agents, ascorbic acid or a combination of citric acid and ascorbic acid was added (0.5% weight of solvent) and mixed thoroughly. The macerate was transferred into plastic containers with minimal headspace. The macerate was sampled and tested via HPLC (high performance liquid chromatography) weekly for a 6-week maceration period and then pressed. The finished extract was continually monitored at week 9, month 2, month 3 and month 6.

The total flavonoids, calculated as a sum of the individual compounds scutellarein, baicalein, scutellarin, dihydrobaicalin, baicalain and chrysin, were monitored over 6 months and were measured using HPLC-UV. Compound identity was confirmed using HPLC-UV/MS. The results are depicted in the FIGURE, which plots total flavonoids for each sample (and a control sample using no heat and no stabilizing agents) at each monitoring time. Heating the macerate extracted a significantly higher amount of flavonoids than no heat (control: 0.628% w/w dry herb; 70° C.: 4.99% w/w). Flavonoids continued to extract well at higher temperatures 80° C. (6.83% w/w) and 90° C. (5.94% w/w), however, stability for all heated and non-heated treatments over 6 months was poor (30.1%-66.4% loss of total flavonoids). Addition of antioxidants (citric acid and ascorbic acid) as well as initial heat (70° C.) of the macerate showed the greatest improvements in the 6-month extract stability (2.4%-10.5% loss in total flavonoids).

While specific embodiments of the present invention have been described, it will be apparent to those skilled in the art that various modifications thereto can be made without departing from the spirit and scope of the invention as defined in the appended claims.

What is claimed is:

1. A composition comprising an extract of *Scutellaria lateriflora* L., said extract produced by subjecting dried aboveground parts of *S. lateriflora* to a solvent consisting of water at a temperature of about 65° C. to about 95° C. and a stabilizing agent comprising ascorbic acid of about 0.45% w/w to about 0.5% w/w for a period of time sufficient to obtain a content of *S. lateriflora* derived flavonoids of at least 10% by weight of total dried extract and wherein degradation of said flavonoids is 10.5% or less after 6 months.

2. The composition of claim 1 wherein said stabilizing agent additionally comprises about 0.05% w/w of citric acid.

3. The composition of claim 1, wherein said content of *S. lateriflora* derived flavonoids of is at least 15% by weight of total dried extract.

4. The composition of claim 1, wherein said content of *S. lateriflora* derived flavonoids is at least 18% by weight of total dried extract.

5. The composition of claim 1, wherein the degradation of said flavonoids is 5% or less after 6 months.

6. The composition of claim 1, wherein the degradation of said flavonoids is 2.5% or less after 6 months.

* * * * *